United States Patent [19]

Lang et al.

[11] Patent Number: 4,898,883

[45] Date of Patent: Feb. 6, 1990

[54] 1-SUBSTITUTED DERIVATIVES OF 4-METHOXY-2,3,6-TRIMETHYLBENZENE, PROCESS FOR THEIR PREPARATION AND MEDICINAL AND COSMETIC COMPOSITIONS CONTAINING THEM

[75] Inventors: Gerard Lang, Saint Gratien; Serge Forestier, Claye-Souilly; Alain Lagrange, Chatou; Braham Shroot, Antibes, all of France

[73] Assignee: L'Oreal, Paris, France

[21] Appl. No.: 75,890

[22] Filed: Jul. 21, 1987

Related U.S. Application Data

[63] Continuation of Ser. No. 765,150, Aug. 13, 1985, abandoned.

[30] Foreign Application Priority Data

Aug. 13, 1984 [LU] Luxembourg ............................ 85502

[51] Int. Cl.[4] ..................... A61K 31/19; A61K 31/21; C07C 65/28
[52] U.S. Cl. ............................ 514/544; 424/DIG. 13; 514/506; 514/532; 514/557; 514/576; 514/721; 514/736; 514/844; 514/859; 514/864; 514/880; 514/881; 514/886; 514/887; 514/946; 514/699; 514/912; 560/8; 560/64; 560/104; 562/405; 562/473; 562/495; 562/510
[58] Field of Search ...................... 560/8, 64, 65, 100, 560/254, 255, 104; 514/576, 557, 859, 861, 863, 864, 844, 880, 881, 886, 887, 506, 557, 576, 699, 532, 717, 725, 726, 739, 946, 947, 970, 972, 544, 576, 699, 721, 736, 912; 562/405, 473, 510, 495; 568/626, 628, 807, 813, 425, 442, 664; 424/DIG. 13

[56] References Cited

U.S. PATENT DOCUMENTS 4,326,055  4/1982  Loeliger ............................. 562/473
4,670,465  6/1987  Guzman et al. .................... 562/473

OTHER PUBLICATIONS

Peter Loeliger et al, European J. Med. Chem.–Chimica Therapeutica, 1980, pp. 9–15.
Lang et al, CA 105–97164d, (1986), "Methoxytrimethylbenzene derivatives".
Loeliger, Chem. Abst. 93–46243e, (1980), "Bicyclic derivatives useful in preparing stibene derivatives".
Loeliger et al, Chem. Abst. 93–18602e (1980), "Arotinoids, a new class of highly active retinoids".
Bouclier et al, Dermatologica, 169, No. 4, (1984), pp. 242–243.
Connor et al, Cancer Research 43, pp. 5174–5177, (1983).

Primary Examiner—Cecilia Shen
Attorney, Agent, or Firm—Cushman, Darby & Cushman

[57] ABSTRACT

The present invention relates to 1-substituted derivatives of 4-methoxy-2,3,6-trimethylbenzene which are useful in cosmetic or pharmaceutical preparations for use in the treamtnet of dermatological complaints connected with a keratinisation disorder, dermatological complaints having an inflammatory and/or immunoalleric component or ophthalmological complaints.

18 Claims, No Drawings

1-SUBSTITUTED DERIVATIVES OF 4-METHOXY-2,3,6-TRIMETHYLBENZENE, PROCESS FOR THEIR PREPARATION AND MEDICINAL AND COSMETIC COMPOSITIONS CONTAINING THEM

This is a continuation of application Ser. No. 765,150 filed Aug. 13, 1985, now abandoned.

BACKGROUND OF THE INVENTION

1. Field of the Invention

The invention relates to 1-substituted derivatives of 4-methoxy-2,3,6-trimethylbenzene, and to a preparative process enabling these novel compounds to be produced. The invention also relates to the use of these compounds in either cosmetics or pharmaceutical preparations in the treatment of dermatological complaints connected with a keratinization (differentiation-proliferation) disorder, in the treatment of dermatological complaints having an inflammatory and/or immuno-allergic component, in the treatment of diseases of degeneration of conjunctive tissue and tumors, in the treatment of rheumatoid psoriasis as well as in an ophthalmological pharmaceutical preparation particularly for treating corneopathies.

These compounds may also be used in the treatment of atopy such as eczema.

2. Description of the Prior Art

The therapeutic activity of vitamin A in its acid, aldehyde or alcohol form is well known in dermatology (see, on this point, the publication "Experientia", volume 34, pages 1105-1119 (1978)); this activity in the treatment of cutaneous proliferations, acne, psoriasis and similar complaints will be referred to below by the generic expression "retinoid type activity".

It is necessary to distinguish between the retinoids and the carotenoids because these groups of products have neither the same toxicological properties nor the same pharmacological properties (see the publication by Richard Peto in "Cancer Surveys" vol. 2, No. 2, 1983 "The marked differences between carotenoids and retinoids: methodological implications for biochemical epidemiology.").

It has been found that products which have a structure similar to vitamin A also have a retinoid type activity, but that the secondary effect of a toxic hypervitaminosis could, in the case of some compounds, be multiplied by a smaller factor than the multiplication factor of the retinoic effect sought (see, on this point, "Eur. J. Med. Chem.-Chimica Therapeutica", Jan.-Feb. 1980, 15, No. 1, pages 9-15); P. Loeliger et al. have described, in this latest publication, a derivative of the formula (I):

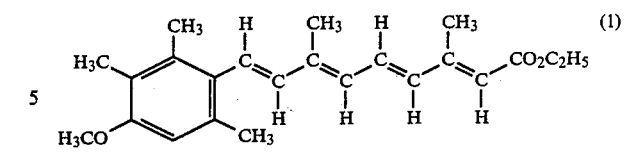

SUMMARY OF THE INVENTION

It has been found, according to this invention, that it is possible to replace the substituent chain in the compound of formula (I) by another substituent chain containing one or two benzene nuclei, without thereby losing the benefit of the retinoic activity of these compounds.

Thus the invention provides a compound which is of formula (II)

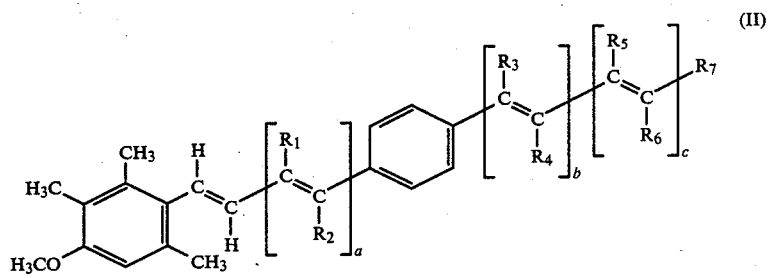

in which a, b and c are each independently 0 or 1;

$R_1$, $R_2$, $R_3$, $R_4$, $R_5$ and $R_6$ are each independently, hydrogen or $C_1$-$C_6$ alkyl, $R_7$ is:

$C\equiv N$;

oxazolinyl:

$CH_2OR_8$ in which $R_8$ is hydrogen, $C_1$-$C_6$ alkyl, $C_2$-$C_6$ mono or polyhydroxyalkyl, cyclopentyl, cyclohexyl, or $OR_8$ denotes tetrahydropyranyl a group of formula (III):

in which $R_9$ is:

(a) hydrogen, $C_1$-$C_6$ alkyl, a group NR'R", in which R' and R" are each independently hydrogen, $C_1$-$C_6$ alkyl, $C_3$-$C_4$ alkenyl, cyclopentyl or cyclohexyl or an optionally substituted aralkyl or aryl group, or R', and R" together with the nitrogen atom to which they are attached form a heterocyclic ring, or

is an amino acid residue or glucosamine residue;

(b) a radical $-OR_{10}$ where $R_{10}$ is hydrogen, a $C_1$-$C_{18}$ alkyl, or $C_2$-$C_6$ mono or polyhydroxyalkyl or isomer or salt thereof.

DETAILED DESCRIPTION OF THE INVENTION

Among the $C_1$–$C_{18}$ alkyl radicals which are particularly capable of being employed as the radical $R_{10}$ mention is made, of methyl, ethyl propyl, 2-ethylhexyl, octyl, dodecyl, hexadecyl and octadecyl radicals.

Among the $C_1$–$C_6$ alkyl radicals which are particularly capable of being employed as the radicals $R_1$ to $R_6$, $R_8$, $R_9$, R' and R'' mention is made of methyl, ethyl, isopropyl, butyl and tert-butyl and, preferably, for $R_1$ to $R_6$, methyl.

Among the substituted or unsubstituted aryl radicals which are particularly capable of being employed as the radicals R' and R'', preference is given to phenyl optionally substituted by a helogen atom, a hydroxyl or a $C_1$–$C_6$ alkoxy group. Among the aralkyl radicals which are particularly capable of being employed as the radicals R' and R'', preference is given to benzyl or phenethyl, which are optionally substituted by a hydroxyl group or an alkoxy group.

When the radicals R' and R'' form a heterocyclic ring with the nitrogen atom to which they are attached, the ring is, preferably, a piperidino, morpholino, piperazino or pyrrolidino ring, or 4-(2-hydroxyethyl)piperazino.

The compounds of formula (II) which are particularly preferred are those of structure

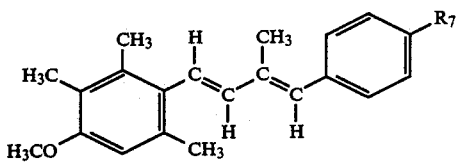

where $R_7$ is as defined above.

The compounds of formula (II) or their isomers may be in the form of their salts; these may be e.g. either salts of zinc, an alkali metal or an alkaline-earth metal or of an organic amine when they contain at least one free acid group, or salts of an inorganic or organic acid, particularly hydrochloride, hydrobromide or citrate, when they contain at least one amine group.

The invention also relates to a process for the preparation of these compounds. This process comprises reacting a compound of formula (IV):

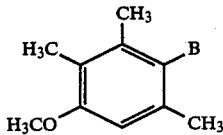

with a compound of formula (V):

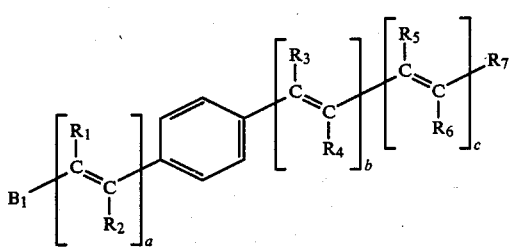

in which $R_1$, $R_2$, $R_3$, $R_4$, $R_5$, $R_6$, $R_7$, a, b and c are defined as in claim 1, provided that $R_7$ cannot be a group of formula (III):

when $R_9$ is hydrogen or a $C_1$ $C_6$ alkyl, one of the groups B and $B_1$ in formulae (IV) and (V) above is a carbonyl group while the other is either (a) a methylenetriarylphosphonium group of formula (VI):

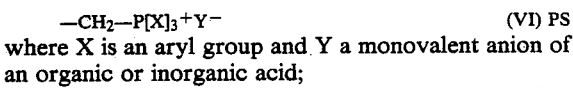

where X is an aryl group and Y a monovalent anion of an organic or inorganic acid;

or (b) a methylenedialkoxyphosphinyl group of formula (VII):

where Z is a $C_{1-C4}$ alkoxy group.

When one of B and $B_1$ denotes a carbonyl group and the other denotes a methylenetriarylphosphonium group, the reaction is preferably carried out in the presence of an alkali metal alcoholate such as sodium methoxide, or in the presence of an alkylene oxide optionally substituted by an alkyl group, optionally in a solvent such as methylene chloride or dimethylformamide. The reaction temperature is from ambient temperature to the boiling point of the reaction mixture.

When one of B and $B_1$ denotes a carbonyl group and the other denotes a methylenedialkoxyphosphinyl group, the reaction is preferably carried out in the presence of a base and, preferably, in the presence of an inert organic solvent; the reaction may be carried out, for example, by using sodium hydride in benzene, toluene, dimethylformamide, tetrahydrofuran, dioxane, 1,2-dimethoxyethane or also by using an alcoholate, for example by using sodium methoxide, in methanol; the reaction is preferably carried out in a temperature range from 0° C. to the boiling point of the reaction mixture. The condensation can also be carried out by using an inorganic base, such as potassium hydroxide or sodium hydroxide, in an organic solvent, such as tetrahydrofuran. A crown-ether capable of complexing the metal cation present in the base, thereby enabling its strength to be increased, can also be added to the reaction mixture.

The compounds of formula (IV) and (V) are known compounds or can be prepared by the use of known methods.

The compounds of formula (II) produced by this process can undergo functional modifications of the substituent $R_7$. Among the functional modifications of this substituent $R_7$, mention is made, for example, of the saponification of a carboxylic acid ester or the reduction of the carboxylic acid ester group to a hydroxymethyl group. The hydroxymethyl group can also be oxidized to a formyl group, or esterified or converted to an ether. Furthermore, a carboxy group may be converted to a salt, an ester, an amide, an alcohol or an acetyl group. A carboxylic acid ester group may be converted to an acetyl group. The acetyl group may be converted to a secondary alcohol group by reduction, and the secondary alcohol group may itself be alkylated or acylated by a known process. All these functional modifications may be produced by processes which are known per se.

The compounds of formula (II) are normally obtained in the form of cis-trans mixtures which can be separated, it required, in a manner known per se, into cis and trans compounds or may be isomerized to wholly trans compounds.

It has been found that the compounds of formula (II) have an activity of a retinoid type and are particularly suitable for treating the dermatological complaints connected with a keratinization (differentiation-proliferation) disorder, and dermatological complaints with an inflammatory and/ or immuno-allergic component, particularly for treating common, comedonian or polymorphous acnes, senile solar acnes and medicamentous or occupational acnes, the extensive and/or severe forms of psoriasis and the other kerathinization disorders, and particularly ichthyoses and ichthyosis states, Darier's disease, palmo-planter keratosis, leucoplasies and leucoplasiform states, lichen planus, and all benign or malignant, severe or extensive dermatological proliferations; they are also active against rheumatoid psoriasis and in the treatment of cutaneous atopy such as eczema. They also find an application in the ophthalmology field, particularly for the treatment of corneopathies.

These compounds exhibit good activity in the ornithin decarboxylase (ODC) inhibition test after induction by "tape stripping" in the hairless rat (Dermatologica 169, No. 4 (1984) "A rapid and Simple Test System for the Evaluation of the Inhibitory Activity of Topical Retinoids on Cellotape Stripping Induced ODC Activity in the Hairless Rat" M. Bouclier et al.).

This test is recognized as a measure of the activity of retinoids on the cellular proliferation phenomena. By way of indication, in this test, the topical application of 25 nmoles/cm$^2$ of the compound of Example 2 has been found to significantly inhibit (60% inhibition) the ODC activity.

The compounds according to the invention show excellent comedolytic activity in the test on the Rhino mouse described by Bonne et al. in International Journal of Cosmetic Science 3, 23–28 (1981).

The testing is carried out on the skin of a Hairless Rhino mouse, recommended as a model for screening comedolytic agents by Van Scott, in 1972, and based on the histological picture.

This method has been reproduced by Bonne, proposing the quantification of the test. In fact, the skin surface of the Rhino mouse shows cyst formations whose narrow orifice d, related to the cyst diameter D, defines, according to Bonne, a characteristic "comedonian profile". On the dorsal and interscapular region, the ration d/D, in the region of 0.4 to 0.7 in the control, rises after a topical application of the substance to be tested, in solution, to $r = d/D \geqq 1$ 15 male or female Hairless Rhino mice aged 2 and a half months at the start of the experiment were divided into three batches:

The first batch is treated with an acetone solution of the substance to be tested at the required concentration. 200 μl of solution are applied on the back, for 5 consecutive days weekly for 3 weeks.

The second batch is treated with an acetone solution of the reference product at a given concentration.

The third batch is treated with acetone.

24 hours after the final application the mice are sacrificed by dislocation of the neck vertebrae. Two fragments of dorsal skin are removed from the treated zone.

Bonne's histological method consists in fixing using Karnovsky, post-fixing dehydrated osmium tetroxide and then embedding in Epon. The blocks are sectioned into 2 μm thickness. The sections are stained with toluidine blue and examined under the microscope. Measurements of d (comedo opening) end D (comedo diameter) (expressed in μm) are made with a semiautomatic image analyser.

According to this protocol, the compounds of Examples 2 and 14 were tested at a concentration of 0.1% in acetone, the reference product being retinoic acid at the same concentration.

The ratio r was found to be equal, respectively, to 1.35±0.04 and 1.11±0.10. In this test, these compounds show an activity which is substantially equal to that of retinoic acid.

The present invention consequently also relates to a novel medicinal composition, intended particularly for the treatment of the abovementioned complaints, characterized in that it comprises, in a pharmaceutically acceptable carrier, at least one compound of formula (II) and/or one of its isomers and/or one of its salts.

When the compounds are employed by a topical route, these compounds are observed to have good activity over a very wide range of dilution; in particular, concentrations of active product ranging from 0.0005% to 2% by weight may be employed. Obviously, it is possible to employ higher concentrations when this is required for a particular therapeutic application; however, the preferred concentrations of active product are between 0.002% and 1% by weight. The topical compositions are advantageously presented in the form of ointments, gels, creams, pomades, powders, tinctures, solutions, suspensions, emulsions, lotions, sprays, dressings, and saturated pads. The compounds are mixed with nontoxic, inert, usually liquid or pasty carriers, which are suitable for treatment by a topical route. The compounds may also be administered by an enteral route.

By oral route, the compounds are typically administered in a proportion of approximately 2 μg up to 2 mg per day and per kg of body weight; an excessive dosage may manifest itself in the form of an A-hypervitaminosis which can be recognized by its symptoms and is capable of raising concern about a hepatic toxicity requiring a biological monitoring of the hepatic function. The required dosage may be administered in one or more doses.

Suitable forms for oral administration are, for example, tablets, gelatin capsules, coated tablets, syrups, suspensions, emulsions, solutions, powders and granules; a preferred method of administration consists in using gelatin capsules, containing from 0.1 mg to approximately 1 mg of active product.

The compounds may also be administered by a parenteral route in the form of solutions or suspensions for intravenous or intramuscular perfusions or injections. In this case, the compounds are administered in a proportion of approximately 2 μg up to 2 mg per day and per kg of body weight; a preferred method of administration consists in employing solutions or suspensions containing from 0.01 to approximately 1 mg of active product per ml.

When the compounds are administered via an ocular route, they are preferably presented in the form of solutions or powders to be diluted for eye lotions.

The pharmaceutically acceptable carrier may incorporate water, gelatin, lactose, starch, talc, vaseline, gum arabic, polyalkylene glycols and magnesium stearate. The tablets, powders, coated tablets, granules or gelatin capsules may contain binders, fillers or carrier powders. The solutions, creams, suspensions, emulsions or syrups may contain diluents, solvents and thickeners.

The compounds also find application in the field of cosmetics, in particular in body hygiene and hair care and particularly in the treatment of acne, seborrheas and hair loss and for regrowth of hair, as well as for the prevention and cure of the harmful action of sunlight and in the treatment of physiologically dry skins.

The present invention consequently also relates to a novel cosmetic composition, characterized in that it comprises, in a cosmetically acceptable carrier, at least one compound of formula (II) and/or one of its isomers and/or one of its salts; this composition may be in the form of e.g. a lotion, gel, cream, soap or shampoo.

The concentration of active product in the cosmetic compositions is from 0.0005% to 2% and, preferably from 0.01% to 1% by weight.

In the treatment of the abovementioned disorders, the compounds, which are employed in the compositions defined above, act by increasing the follicular epithelial production of the non-adhesive cells, thus dislodging and expelling the content of the acne comedo. The compounds reduce the size of the sebaceous glands and partly inhibit sebum secretion.

The compositions may contain inert or even pharmacodynemically or cosmetically active additives and, in particular:

hydrating agents such as thiamorpholinone and its derivatives, or urea antiseborrhoes or antiacne agents such as those described in French Patents 1,472,021, 1,505,874, 1,560,250, 2,002,461, 2,035,799, 2,011,940, 2,060,407, 2,126,996, 2,133,991, 2,133,992, 2,139,876, 2,158,018, 2,296,406, 2,428,436, 2,468,362, 2,446,277 or 2,447,189, and U.S. Pat. No. 2,332,418, and, in particular, 5-carboxymethylcysteine, 5-benzylcysteamine, their salts and their derivatives, thioxolone or benzoyl peroxide, antibiotics such as erythromycin and its esters, for example those described in U.S. Pat. No. 2,862,921 or French patent application No. 85/05,785, neomycin, tetracyclines, or 4,5-polymethylene-3-isothiazolinones such as described in French Pat. No. 2492376.

agents promoting the regrowth of hair, such as minoxidil (2,4-diamino-6-piperidino-3-pyrimidine oxide) and its derivatives, diazoxide (3-chloro-methyl-1,2,4-benzothiadiazine-1,1-dioxide), phenyltoin (5,5-diphenyl-2,4-imidazolidinedione) oxypropanium iodide or anthralin and its derivatives, antiinflammatory agents (steroids and nonsteriods)

carotenoids and particularly β-carotene, antiposrietic agents such as eicosa-5,8,11,14-tetraynoic and 5,8,11-triynoic acids, their esters and their amides, anthralin and its derivatives, such as those described in French Pat. Nos.: 2,113,952, 2,492,372, 2,492,373, 2,495,934, 2,499,556, or French patent applications 84/09, 203, and 84/10,324 or U.S. Pat. No. 4,299,846, naphthalene and naphthoquinone derivatives such as those described in U.S. Pat. No. 4,229,478, European Pat. No. 7,985 or J.I.D. 84 (4) 358 (1985).

The compositions may also contain flavoring agents, preserving agents stabilizers, moisture-controlling agents, pH-controlling agents, osmotic-pressure modifiers, emulsifiers, UV-A and UV-B screening agents such as those described in French Pat. Nos. 1,179,387 or 2,528,420 and antioxidants such as α-tocopherol, butylated hydroxyanisole or butylated hydroxytoluene.

To further illustrate the invention several examples of implementation will now be described. All the compounds prepared in Examples 1 to 14 have a trans structure.

EXAMPLE 1

Preparation of the Compound of Formula:

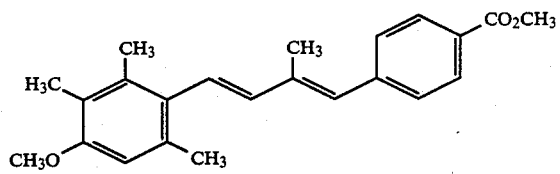

15 cm³ of butyllithium are added at −70° C. to a suspension of 10.1 g of 4-methoxy-2,3,6-trimethylbenzyltriphenylphosphonium bromide in 50 cm³ of tetrahydrofuran. The temperature is allowed to rise to −30° C. over 30 min and then a solution of 4α-methoxycarbonylmethylcinnamaldehyde in the minimum quantity of tetrahydrofuran is added at −70° C. The reaction mixture is stirred for one hour at −70° C. and then allowed to return to ambient temperature. It is poured onto an aqueous solution of ammonium chloride and extracted with ether. After drying of the organic phase the product is purified by chromatography on silica gel (solvent=hexane/ethyl acetate 97.5/2.5) and is then recrystallized from ethanol. 3.4 g of a compound with the following characteristics are obtained:

Melting point: 120° C.

| UV spectrum: | $\lambda$ max = 326 nm | (chloroform) |
| --- | --- | --- |
| | $\epsilon$ = 28000 | |

| Elemental analysis: | C | H | O |
| --- | --- | --- | --- |
| Calculated | 78.83 | 7.48 | 13.70 |
| Found | 78.67 | 7.53 | 13.88 |

EXAMPLE 2

Preparation of the Compound of Formula:

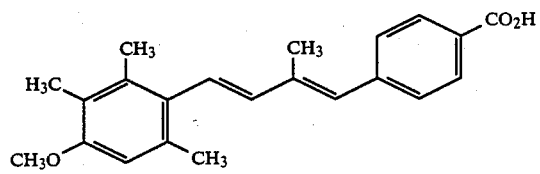

A solution of 1.8 g of the compound obtained in Example 1, dissolved in 25 cm³ of ethanol and 5 cm³ of water containing 1 g of potassium hydroxide is heated at reflux for one hour. It is cooled and acidified with 2 N hydrochloric acid. After extraction with ether, evaporation of the solvent and recrystallization from acetone, 1.2 g of a product with the following characteristics is obtained:

Melting point: 224° C.

| UV spectrum: | λmax = 326 nm | (chloroform) |
|---|---|---|
| | ε = 27600 | |

| Elemental Analysis: | | | |
|---|---|---|---|
| | C | H | O |
| Calculated | 78.54 | 7.19 | 14.26 |
| Found | 78.55 | 7.22 | 14.12 |

EXAMPLE 3

Preparation of the Compound of Formula:

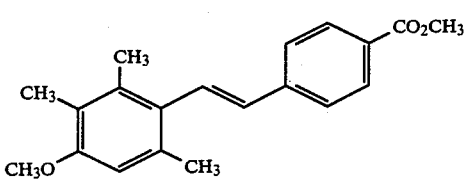

This compound is obtained according to the operating procedure described in Example 1, in which 4-α-methoxycarbonylmethylcinnamaldehyde is replaced by 4-methoxycarbonylmethylcinnamaldehyde.

The product obtained is purified by recrystallization from hexane. It has the following properties:

Melting point: 104° C.

| UV spectrum: | λmax = 320 nm | (methanol) |
|---|---|---|
| | ε = 19600 | |

| Elemental analysis: | | | |
|---|---|---|---|
| | C | H | O |
| Calculated | 77.39 | 7.14 | 15.46 |
| Found | 77.26 | 7.13 | 15.25 |

EXAMPLE 4

Preparation of the Compound of Formula:

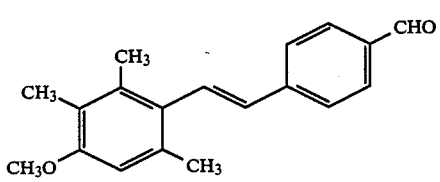

20 cm³ of a 1.6 M solution of butyllithium are added at −70° C. to a suspension of 15.2 g of 4-methoxy-2,3,6-trimethylbenzyltriphenylphosphonium bromide in 50 cm³ of tetrahydrofuran. The temperature is allowed to rise to 0° C. and the mixture is stirred for 30 min at this temperature. It is cooled to −70° C. and a solution of 5.4 g of 4-dimethoxymethylbenzaldehyde in 2 cm³ of dichloromethane is added dropwise. The mixture is stirred at −70° C. for 1 h 30 and then allowed to return to ambient temperature. 10 cm³ of 1 N hydrochloric acid are added. The product is extracted with ether. After evaporation of the solvent and recrystallization from isopropanol, 4.4 g of pale yellow crystals are obtained. This product has the following properties:

Melting point: 104° C.

| UV spectrum: | λmax = 335 nm | (ethanol) |
|---|---|---|
| | ε = 18000 | |

| Elemental analysis | | | |
|---|---|---|---|
| | C | H | O |
| Calculated | 81.40 | 7.19 | 11.41 |
| Found | 81.21 | 7.15 | 11.57 |

EXAMPLE 5

Preparation of the Compound of Formula:

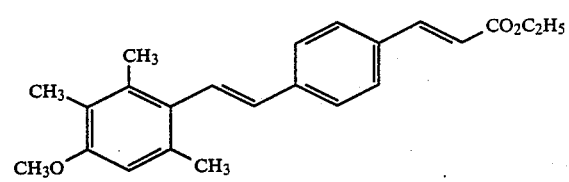

2.87 g of triethyl phosphonoacetate are dissolved in 15 cm³ of tetrahydrofuran. 1.3 g of ground potassium hydroxide is added and stirred at ambient temperature for 15 min. A solution of 3 g of the aldehyde obtained in Example 4 in 15 cm³ of tetrahydrofuran is added dropwise. The reaction mixture is stirred for one hour and then diluted with toluene. It is filtered through silica. After recrystallization from ethanol, 2 g of yellow crystals are obtained. This product has the following properties:

Melting Point: 115° C.

| UV spectrum: | λmax = 335 nm | (ethanol) |
|---|---|---|
| | ε = 29000 | |

| Elemental analysis: | | | |
|---|---|---|---|
| | C | H | O |
| Calculated | 78.83 | 7.45 | 13.70 |
| Found | 78.79 | 7.52 | 13.60 |

EXAMPLE 6

Preparation of the Compound of Formula:

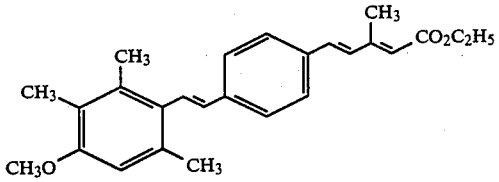

This compound is obtained according to the operating procedure described in Example 5 in which triethyl phosphonoacetate is replaced by diethyl 3-ethoxycarbonyl-2-methylpropen-2-ylphosphonate.

The product obtained is purified by recrystallization from isopropanol; it has the following properties:

Melting point: 101° C.

λmax = 355 nm (chloroform)

| UV spectrum: | $\epsilon = 42000$ | | |
|---|---|---|---|
| | Elemental analysis: | | |
| | C | H | O |
| Calculated | 79.97 | 7.74 | 12.29 |
| Found | 79.87 | 7.71 | 12.25 |

EXAMPLE 7

Preparation of the Compound of Formula:

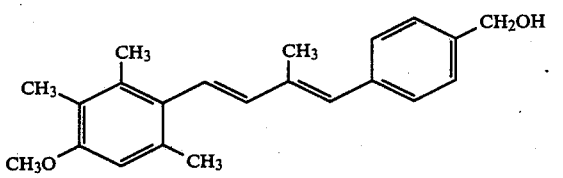

A solution of 1 g of lithium aluminium hydride in 30 cm³ of tetrahydrofuran is cooled to 0° C. A solution of 8 g of the compound obtained in Example 1 in 40 cm³ of tetrahydrofuran is added slowly between 5° and 10° C. The mixture is kept at this temperature for 1 hour and then 5 cm³ of ethyl acetate are added. After adding water, extracting with ether, evaporating off the solvent and recrystallizing from hexane, 5.4 g of white crystals are obtained. This product has the following properties:

Melting point: 89° C.

| UV spectrum: | $\lambda max = 302$ nm | (ethanol) | |
|---|---|---|---|
| | $\epsilon = 30000$ | | |
| | Elemental analysis: | | |
| | C | H | O |
| Calculated | 81.95 | 8.13 | 9.92 |
| Found | 81.90 | 8.15 | 9.95 |

EXAMPLE 8

Preparation of the Compound of Formula:

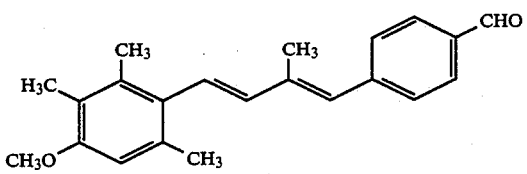

4.5 g of the compound obtained in Example 7 are dissolved in 90 cm³ of ether. A suspension of 8 g of manganese dioxide in 90 cm³ of hexane is added. The mixture is stirred for 2 hours and then 8 g of manganese dioxide are added again. After an additional 3 hours' stirring the mixture is filtered through celite. The solvent is evaporated off and the residue is chromatographed on silica gel (eluant: toluene). 3.1 g of yellow crystals are obtained. This product has the following properties:

Melting point: 65° C.

| UV spectrum: | $\lambda max = 345$ nm | (chloroform) |
|---|---|---|

| | $\epsilon = 24500$ | | |
|---|---|---|---|
| | Elemental analysis: | | |
| | C | H | O |
| Calculated | 82.46 | 7.55 | 9.99 |
| Found | 82.35 | 7.52 | 10.02 |

EXAMPLE 9

Preparation of the Compound of Formula:

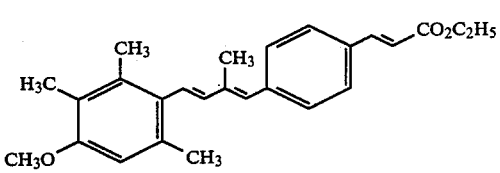

This compound is obtained according to the operating procedure described in Example 5, in which the aldehyde obtained in Example 4 is replaced by the aldehyde obtained in Example 8. The product is recrystallized from ethanol; it has the following properties:

Melting point: 93° C.

| UV spectrum: | $\lambda max = 348$ nm | (chloroform) | |
|---|---|---|---|
| | $\epsilon = 35000$ | | |
| | Elemental analysis: | | |
| | C | H | O |
| Calculated | 79.97 | 7.74 | 12.29 |
| Found | 79.85 | 7.78 | 12.10 |

EXAMPLE 10

Preparation of the Compound of Formula:

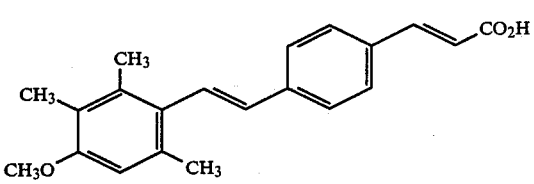

This compound is obtained by hydrolysis of the compound described in Example 5 according to the operating procedure described in Example 2.

The product is recrystallized from a mixture of water and acetone (50/50); it has the following properties:

Melting point: 184° C.

| UV spectrum: | $\lambda max = 348$ nm | (chloroform) | |
|---|---|---|---|
| | $\epsilon = 28500$ | | |
| | C | H | O |
| Calculated | 78.23 | 6.88 | 14.89 |
| Found | 78.47 | 6.95 | 14.85 |

EXAMPLE 11

Preparation of the Compound of Formula:

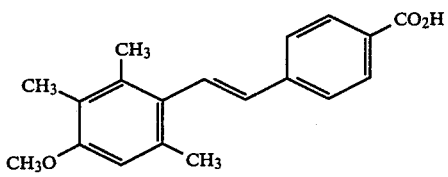

This compound is obtained by hydrolysis of the compound described in Example 3 according to the operating procedure described in Example 2. The product is recrystallized from acetic acid; it has the following properties:

Melting point: 214° C.

| UV spectrum: | $\lambda max = 313$ nm | (methanol) |
| --- | --- | --- |
|  | $\epsilon = 19100$ |  |

| Elemental analysis: | | | |
| --- | --- | --- | --- |
|  | C | H | O |
| Calculated | 77.00 | 6.80 | 16.19 |
| Found | 76.94 | 6.74 | 16.21 |

EXAMPLE 12

Preparation of the Compound of Formula:

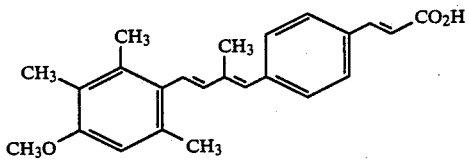

This compound is obtained by hydrolysis of the compound described in Example 9 according to the operating procedure described in Example 2.

The product is recrystallized from a mixture of water and acetone (50/50); it has the following properties:

Melting point: 193° C.

| UV spectrum: | $\lambda max = 350$ nm | (chloroform) |
| --- | --- | --- |
|  | $\epsilon = 33000$ |  |

| Elemental analysis: | | | |
| --- | --- | --- | --- |
|  | C | H | O |
| Calculated | 79.53 | 7.23 | 13.24 |
| Found | 79.43 | 7.25 | 13.06 |

EXAMPLE 13

Preparation of the Compound of Formula:

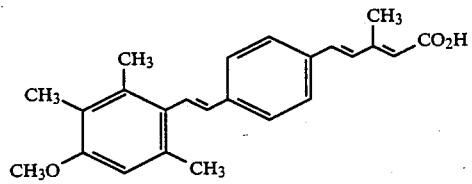

This compound is obtained by hydrolysis of the compound described in Example 6 according to the operating procedure described in Example 2.

The product is recrystallized from acetone; it has the following properties:

Melting point: 208° C.

| UV spectrum: | $\lambda max = 353$ nm | (chloroform) |
| --- | --- | --- |
|  | $\epsilon = 39500$ |  |

| Elemental analysis: | | | |
| --- | --- | --- | --- |
|  | C | H | O |
| Calculated | 79.53 | 7.23 | 13.24 |
| Found | 79.38 | 7.29 | 13.16 |

EXAMPLE 14

Preparation of the Compound of Formula:

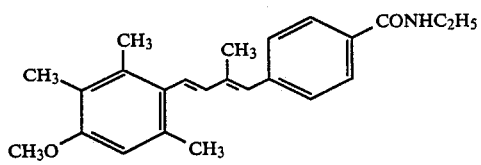

1.39 g of the compound obtained in Example 2 and 0.8 g of carbonyldiimidazole are heated for 3 hours at 50° C. in 40 cm³ of dimethylformamide. The mixture is allowed to cool and 2 cm³ of ethylamine are added. After one hour at ambient temperature the mixture is diluted with 100 cm³ of ethyl acetate. The organic phase is washed with water, dried over sodium sulphate and filtered through silica gel. 1.42 g of a crude product is obtained which, after recrystallization from ethanol, has the following properties:

Melting point: 162° C.

| UV spectrum: | $\lambda max = 322$ nm | (chloroform) |
| --- | --- | --- |
|  | $\epsilon = 27650$ |  |

| Elemental analysis: | | | | |
| --- | --- | --- | --- | --- |
|  | C | H | N | O |
| Calculated | 79.30 | 8.04 | 3.85 | 8.80 |
| Found | 79.13 | 8.14 | 3.79 | 8.86 |

EXAMPLE 15

The following formulation, intended to be packaged in a gelatin capsule is prepared:

| Compound of Example 1 | 0.050 g |
| --- | --- |
| Corn starch | 0.060 g |
| Lactose q.s. | 0.300 g |

The gelatin capsules employed consist of gelatin, titanium oxide and a preserving agent.

1 to 3 gelatin capsules are administered daily to an adult individual for the treatment of psoriasis and a significant improvement is noted after approximately 30 days.

EXAMPLE 16

A gel is prepared by producing the following formulation:

| Compound of Example 2 | 0.025 g |
| --- | --- |
| Erythromycin base | 4.000 g |
| Butylated hydroxytoluene | 0.050 g |
| Hydroxypropylcellulose, sold by the Hercules Company under the name of "Klucel HF" | 2.000 g |
| Ethanol (95°) q.s. | 100.000 g |

This gel is applied to a skin with dermatitis or a skin with acne 1 to 3 times per day and a significant improvement is noted after a period ranging from 6 to 12 weeks depending on the severity of the case treated.

EXAMPLE 17

A 0.10% solution is prepared by producing the following formulation:

| Compound of Example 2 | 0.1 g |
| --- | --- |
| Polyethylene glycol (molecular mass × 400) | 80.0 g |
| Ethanol (95°) q.s. | 100.0 g |

This solution is applied to a skin with acne 1 to 3 times per day and a significant improvement is noted after a period ranging from 6 to 12 weeks depending on the severity of the case treated.

EXAMPLE 18

An antiseborrheic lotion is prepared by producing the following formulation:

| Compound of Example 4 | 0.025 g |
| --- | --- |
| Propylene glycol | 5.000 g |
| Butylated hydroxytoluene | 0.100 g |
| Ethanol (95°) q.s. | 100.000 g |

This lotion is applied twice daily and a significant improvement is noted after a period ranging from 2 to 6 weeks.

EXAMPLE 19

An antiseborrheic cream is prepared by producing the following formulation:

| Polyoxyethylene stearate (40 moles of EO) sold under the name of Myrj 52 by Atlas | 4 g |
| --- | --- |
| Mixture of sorbitan and sorbitol Lauric esters, polyoxyethylenated with 20 moles of EO sold under the name of Tween 20 by Atlas | 1.8 g |
| Mixture of glycerol mono and distearate sold under the name of Geleol by Gattefosse | 4.2 g |
| Propylene glycol | 10 g |
| Butylated hydroxyanisole | 0.01 g |
| Butylated hydroxytoluene | 0.02 g |
| Cetyl-stearyl alcohol | 6.2 g |
| Preserving agents | q.s |
| Perhydrosqualene | 18 g |
| Mixture of caprylic/capric triglycerides sold under the name Miglyol 812 by Dynamit Nobel | 4 g |
| S—Carboxymethyl cysteine | 3 g |
| 99% triethanolamine | 2.5 g |
| Compound of Example 14 | 0.02 g |
| Water q.s. | 100 g |

EXAMPLE 20

An antiseborrheic cream is prepared by producing the following formulation:

| Polyoxyethylene stearate (40 moles of EO), sold under the name of Myrj 52 by Atlas | 4 g |
| --- | --- |
| Mixture of sorbitan and sorbitol Lauric esters, polyoxyethylenated with 20 moles of EO sold under the name of Tween 20 by Atlas | 1.8 g |
| Mixture of glycerol mono and distearate sold under the name of Geleol by Gattefosse | 4.2 g |
| Propylene glycol | 10 g |
| Butylated hydroxyanisole | 0.01 g |
| Butylated hydroxytoluene | 0.02 g |
| Cetyl-stearyl alcohol | 6.2 g |
| Preserving agents | q.s |
| Perhydrosqualene | 18 g |
| Mixture of caprylic-capric triglycerides sold under the name of Miglyol 812 by Dynamit Nobel | 4 g |
| 2-Benzylthioethylammonium 5-amino-5-carboxy-3-thiapentanoate | 3 g |
| Compound of Example 14 | 0.02 g |

EXAMPLE 21

An anhydrous lotion is prepared by mixing the following ingredients:

| Ethanol | 45 g |
| --- | --- |
| Propylene glycol | 44.85 g |
| Polytetrahydrofuran dimethyl ether | 10 g |
| Compound of Example 2 | 0.1 g |
| Butylated hydroxytoluene | 0.05 g |

EXAMPLE 22

A screen gel is prepared by mixing the following ingredients:

| Ethyl alcohol | 44 g |
| --- | --- |
| Propylene glycol | 44.15 g |
| Acrylic acid polymer sold under the name "Carbopol 940" by the Goodrich Chemical Co. | 1 g |
| 99% triethanolamine | 0.5 g |
| Butylated hydroxyanisole | 0.01 g |
| Butylated hydroxytoluene | 0.02 g |
| Purified water | 10 g |
| Compound of Example 2 | 0.02 g |
| 3,3'-Terephthalylidene-10,10'-dicamphosulphonic acid dihydrate | 0.5 g |

EXAMPLE 23

An antiacne cream is prepared by mixing the following ingredients:

| Mixture of polyethylene glycol (75 moles) and glycerol stearates, sold under the name of Gelot 64 by Gattefosse | 15 g |
| --- | --- |
| Kernel oil polyoxyethylenated with 6 moles of EO, sold under the name of Labrafil M 2130 CS by Gattefosse | 8 g |
| Perhydrosqualene | 10 g |
| Colorant | q.s |
| Preserving agents | q.s |
| Perfumes | q.s |
| Thioxolone | 0.4 q.s |
| Polyethylene glycol mol. wt. 400 | 8 g |
| Purified water | 58.5 g |
| Disodium salt of ethylenediaminetetraacetate | 0.05 g |
| Compound of Example 2 | 0.05 g |

EXAMPLE 24

A lotion for stimulating regrowth of hair is prepared by mixing the following ingredients:

| | |
|---|---|
| Propylene glycol | 20 g |
| Ethanol | 34.92 g |
| Polyethylene glycol mol. wt. 400 | 40 g |
| Water | 4 g |
| Butylated hydroxyanisole | 0.01 g |
| Butylated hydroxytoluene | 0.02 g |
| Compound of Example 2 | 0.05 g |
| Minoxidil | 1 g |

EXAMPLE 25

An antiacne cream is prepared by mixing the following ingredients:

| | |
|---|---|
| Polyoxyethylene (40 moles of EO) stearate sold under the name of Myrj 52 by Atlas | 4 g |
| Mixture of sorbitan and sorbitol Lauric esters, polyoxyethylenated with 20 moles of EO, sold under the name of Tween 20 by Atlas | 1.8 g |
| Mixture of glycerol mono and distearate | 4.2 g |
| Propylene glycol | 10 g |
| Butylated hydroxyanisole | 0.01 g |
| Butylated hydroxytoluene | 0.02 g |
| Cetyl-stearyl alcohol | 6.2 g |
| Preserving agents | q.s |
| Polytetrahydrofuran dimethyl ether | 18 g |
| Mixture of caprylic-capric triglycerides, sold under the name of Miglyol 812 by Dynamit Nobel | 4 g |
| Compound of Example 14 | 0.02 g |
| Water q.s. | 100 g |

EXAMPLE 26

An antiacne gel is prepared by producing the following formulation:

| | |
|---|---|
| Compound of Example 14 | 0.05 g |
| Isopropyl alcohol | 40 g |
| Acrylic acid polymer sold under the name "Carbopol 940" by Goodrich Chemical Co. | 1 g |
| 99% triethanolamine | 0.6 g |
| Butylated hydroxyanisole | 0.01 g |
| Butylated hydroxytoluene | 0.02 g |
| Thioxolone | 0.5 g |
| Propylene glycol | 8 g |
| Purified water q.s. | 100 g |

EXAMPLE 27

A screening cream is prepared by producing the following formulation:

| | |
|---|---|
| Polyoxyethylene (40 moles of EO) stearate, sold under the name of Myrj 52 by Atlas | 4.4 g |
| Cetyl-stearyl alcohol | 6.2 g |
| Mixture of glycerol mono and distearate (Geleol) | 4.3 g |
| Butylated hydroxyanisole | 0.05 g |
| Butylated hydroxytoluene | 0.05 g |
| Xanthane gum | 0.25 g |
| Isopropyl myristate | 4 g |
| Compound of Example 14 | 0.1 g |
| 3,3'-Terephthalylidene-10,10'-dicamphosulphonic acid dihydrate | 2 g |
| 99% triethanolamine | 1 g |
| Demineralized water q.s. | 100 g |

EXAMPLE 28

A lotion for the regrowth of hair is prepared by mixing the following ingredients:

| | |
|---|---|
| Propylene glycol | 13.96 g |
| Polyethylene glycol mol. wt. 300 | 40 g |
| Polyethylene glycol mol. wt. 150U | 32 g |
| Isopropanol | 12 g |
| Butylated hydroxyanisole | 0.01 g |
| Butylated hydroxytoluene | 0.02 g |
| Compound of Example 14 | 0.01 g |
| Minoxidil | 2 g |

EXAMPLE 29

This is an antiacne kit comprising two parts:

(a) A gel is prepared by producing the following formulation:

| | |
|---|---|
| Ethyl alcohol | 48.4 g |
| Propylene glycol | 50 g |
| Acrylic acid polymer sold under the name "Carbopol 940" by Goodrich Co. | 1 g |
| 99% diisopropanolamine | 0.3 g |
| Butylated hydroxyanisole | 0.05 g |
| Butylated hydroxytoluene | 0.05 g |
| α-Tocopherol | 0.1 g |
| Compound of Example 14 | 0.1 g |

In this part, the compound of Example 14 may be replaced by that of Example 2.

(b) A gel is prepared by producing the following formulation:

| | |
|---|---|
| Ethyl alcohol | 5 g |
| Propylene glycol | 5 g |
| Disodium salt of ethylenediaminetetraacetic acid | 0.05 g |
| Acrylic acid polymer sold under the name "Carbopol 940" by Goodrich Chemical Co. | 1 g |
| 99% triethanolamine | 1 g |
| Sodium Lauryl sulphate | 0.1 g |
| Purified water | 75.05 g |
| 25% aqueous benzoyl peroxide | 12.8 g |

The two gels are to be mixed extemporaneously, weight for weight.

It is obvious that the examples described above are not restrictive in any manner and can give rise to any desirable modifications, without departing thereby from the scope of the invention.

We claim:

1. A compound having the formula (II)

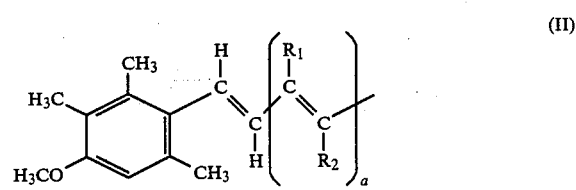

-continued

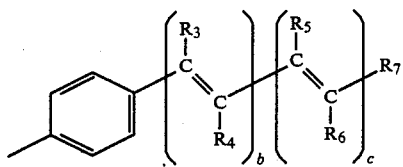

wherein
a is 1 and b and c, each independently, are 0 or 1;
$R_1$, $R_2$, $R_3$, $R_4$, $R_5$ and $R_6$, each independently, are selected from the group consisting of hydrogen and $C_1-C_6$ alkyl;
$R_7$ is selected from the group consisting of (i) —$CH_2OR_8$ wherein $R_8$ is selected from the group consisting of hydrogen, $C_1-C_6$ alkyl, $C_2-C_6$ monohydroxyalkyl, $C_2-C_6$ polyhydroxyalkyl, cyclopentyl and cyclohexyl and (ii) a group of the formula

wherein $R_9$ is hydrogen —$OR_{10}$ wherein $R_{10}$ is selected from the group consisting of hydrogen, $C_1-C_{18}$ alkyl, $C_2-C_6$ monohydroxyalkyl and $C_2-C_6$ polyhydroxyalkyl,
or an isomer or salt thereof.

2. The compound of claim 1 wherein $R_1$, $R_2$, $R_3$, $R_4$, $R_5$ and $R_6$, each independently, are selected from the group consisting of hydrogen and methyl, and $R_7$ is selected from the group consisting of carboxy, alkoxy carbonyl, formyl and hydroxymethyl.

3. The compound of claim 1 having the formula

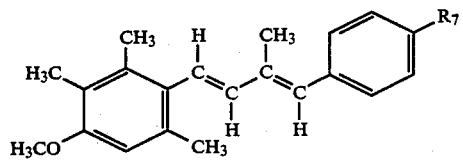

wherein $R_7$ has the meaning given in claim 1.

4. A pharmaceutical composition comprising in a pharmaceutically acceptable carrier at least one compound of formula II of claim 1 in an amount effective to treat dermatologic complaints.

5. The pharmaceutical composition of claim 4 in a form suitable for topical administration, wherein said compound of formula II is present in an amount ranging from 0.0005 to 2 weight percent.

6. The pharmaceutical composition of claim 5 wherein said compound of formula II is present in an amount ranging from 0.002 to 1 weight percent.

7. The pharmaceutical composition of claim 5 in the form of an ointment, gel, cream, pomade, powder, tincture, solution, suspension, emulsion, lotion, spray, dressing or saturated pad.

8. The pharmaceutical composition of claim 6 in a form suitable for enteral administration.

9. The pharmaceutical composition of claim 8 in the form of gelatin capsules containing from 0.1 mg to 1 mg of the compound of formula II.

10. The pharmaceutical composition of claim 6 in the form of a solution or suspension suitable for parenteral administration.

11. The pharmaceutical composition of claim 10 which contains, per ml of solution or suspension, from 0.01 to 1 mg of the compound of formula II.

12. The pharmaceutical composition of claim 6 in a form suitable for ocular administration.

13. The pharmaceutical composition of claim 6 which also contains at least one member selected from the group consisting of water, gelatin, lactose, starch, talc, liquid petrolatum, gum arabic, polyalkylene glycol, magnesium stearate, diluent, solvent and thickener.

14. The pharmaceutical composition of claim 6 which also contains at least one of an inert or pharmacodynamically active additive selected from the group consisting of a hydrating agent, an antiseborrheic agent, an antiacne agent, an antibiotic, an agent for promoting regrowth of hair, an anti-inflammatory agent, a carotenoid, an antipsoriatic agent, a flavoring agent, a preserving agent, a stabilizer, a moisture controlling agent, a pH controlling agent, an osmotic pressure modifier, an emulsifier, a UV-A screening agent, a UV-B screening agent and an antioxidant.

15. A cosmetic composition comprising in a cosmetically acceptable carrier, at least one compound of formula II of claim 1 in an amount effective for use in body hygiene and hair care, for the treatment of acne, seborrhea and hair loss, for regrowth of hair and for protection against damage by sunlight.

16. The cosmetic composition of claim 15 wherein the compound of formula II is present in an amount ranging from 0.0005 to 2 weight percent.

17. The cosmetic composition of claim 15 in the form of a lotion, gel, cream, soap or shampoo.

18. The cosmetic composition of claim 15 which also contains at least one of an inert or cosmetically active additive selected from the group consisting of a hydrating agent, an antiseborrheic agent, an antiacne agent, an antibiotic, an agent for promoting regrowth of hair, an anti-inflammatory agent, a carotenoid, an antipsoriatic agent, a flavoring agent, a preserving agent, a stabilizer, a moisture controlling agent, a pH controlling agent, an osmotic pressure modifier, an emulsifier, a UV-A screening agent, a UV-B screening agent and an antioxidant.

* * * * *